(12) United States Patent
Jonsson et al.

(10) Patent No.: US 8,007,544 B2
(45) Date of Patent: Aug. 30, 2011

(54) LOW PROFILE PROSTHETIC FOOT

(75) Inventors: Orn Ingvi Jonsson, Reykjavik (IS); Christophe Guy Lecomte, Reykjavik (IS); Arinbjorn Viggo Clausen, Reykjavik (IS); Heidrun Gigja Ragnarsdottir, Reykjavik (IS)

(73) Assignee: Ossur HF, Reykjavík (IS)

( * ) Notice: Subject to any disclaimer, the term of this patent is extended or adjusted under 35 U.S.C. 154(b) by 126 days.

(21) Appl. No.: 10/642,125

(22) Filed: Aug. 15, 2003

(65) Prior Publication Data
US 2005/0038524 A1 Feb. 17, 2005

(51) Int. Cl.
*A61F 2/62* (2006.01)
*A61F 2/66* (2006.01)
(52) U.S. Cl. .............................. 623/38; 623/55
(58) Field of Classification Search ............ 623/38, 623/52, 53, 55
See application file for complete search history.

(56) References Cited

U.S. PATENT DOCUMENTS

| | | |
|---|---|---|
| 25,238 A | 8/1859 | Bly |
| 53,931 A | 4/1866 | Weston et al. |
| 56,983 A | 8/1866 | Nicholas |
| 57,666 A | 9/1866 | Bly |
| 368,580 A | 8/1887 | Frees |
| 487,697 A | 12/1892 | Ehle |
| 534,198 A | 2/1895 | Chapman |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 4,007,497 A | 2/1977 | Haupt |
| 4,360,931 A | 11/1982 | Hampton |
| 4,387,472 A | 6/1983 | Wilson |
| 4,547,913 A | 10/1985 | Phillips |
| 4,718,913 A | 1/1988 | Voisin |

(Continued)

FOREIGN PATENT DOCUMENTS

CA 2234362 4/1998

(Continued)

OTHER PUBLICATIONS

Ohio Willow Wood Company: Carbon Copy System III brochure, 5 pages.*

(Continued)

*Primary Examiner* — David H. Willse
(74) *Attorney, Agent, or Firm* — Knobbe Martens Olson & Bear, LLP

(57) ABSTRACT

A low profile prosthetic foot comprises a foot member extending at an incline from an anterior portion to a posterior portion thereof and configured to flex during motion, and an adapter mounted solely at a posterior section thereof to the posterior portion of the foot member so that the adapter's anterior section can move relative to the foot member and "roll-up" onto the foot member during motion.

11 Claims, 11 Drawing Sheets

U.S. PATENT DOCUMENTS

| | | | |
|---|---|---|---|
| 4,822,363 A | 4/1989 | Phillips |
| 4,892,553 A | 1/1990 | Prahl |
| 4,892,554 A | 1/1990 | Robinson |
| 4,959,073 A | 9/1990 | Merlette |
| 5,019,109 A | 5/1991 | Voisin |
| 5,037,444 A | 8/1991 | Phillips |
| 5,062,859 A | 11/1991 | Naeder |
| 5,116,384 A | 5/1992 | Wilson et al. |
| 5,139,525 A | 8/1992 | Kristinsson |
| 5,156,631 A | 10/1992 | Merlette |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,290,319 A | 3/1994 | Phillips |
| 5,376,133 A | 12/1994 | Gramnas |
| 5,376,141 A | 12/1994 | Phillips |
| 5,387,246 A | 2/1995 | Phillips |
| 5,443,527 A | 8/1995 | Wilson |
| 5,443,529 A | 8/1995 | Phillips |
| 5,509,938 A | 4/1996 | Phillips |
| 5,653,767 A | 8/1997 | Allen et al. |
| 5,701,686 A | 12/1997 | Berr et al. |
| 5,728,177 A | 3/1998 | Phillips |
| 5,800,569 A | 9/1998 | Phillips |
| 5,897,594 A | 4/1999 | Martin et al. |
| 5,899,944 A | 5/1999 | Phillips |
| 5,941,913 A | 8/1999 | Woolnough et al. |
| 5,957,981 A | 9/1999 | Gramnas |
| 5,993,488 A | 11/1999 | Phillips |
| 6,071,313 A | 6/2000 | Phillips |
| 6,099,572 A | 8/2000 | Mosler et al. |
| 6,129,766 A | 10/2000 | Johnson et al. |
| 6,165,227 A | 12/2000 | Phillips |
| 6,206,934 B1 | 3/2001 | Phillips |
| 6,241,776 B1 | 6/2001 | Christensen |
| 6,261,324 B1 | 7/2001 | Merlette |
| 6,280,479 B1 | 8/2001 | Phillips |
| 6,350,286 B1 | 2/2002 | Atkinson et al. |
| 6,387,134 B1 | 5/2002 | Parker |
| 6,398,818 B1 | 6/2002 | Merlette et al. |
| 6,402,790 B1 | 6/2002 | Celebi |
| 6,443,993 B1 | 9/2002 | Koniuk |
| 6,443,995 B1 | 9/2002 | Townsend et al. |
| 6,596,029 B1 | 7/2003 | Gramnas |
| 6,663,673 B2 | 12/2003 | Christensen |
| 6,712,860 B2 | 3/2004 | Rubie et al. |
| 6,719,807 B2 | 4/2004 | Harris |
| 6,767,370 B1 * | 7/2004 | Mosler et al. ............ 623/55 |
| 6,793,683 B1 | 9/2004 | Laghi |
| 6,855,170 B2 | 2/2005 | Gramnas |
| 6,899,737 B1 | 5/2005 | Phillips |
| 6,969,408 B2 | 11/2005 | Lecomte |
| 7,052,519 B1 | 5/2006 | Gramnas |
| 7,108,723 B2 | 9/2006 | Townsend et al. |
| 7,279,011 B2 | 10/2007 | Phillips |
| 7,347,877 B2 | 3/2008 | Clausen et al. |
| 2002/0013628 A1 | 1/2002 | Harris |
| 2002/0040249 A1 | 4/2002 | Phillips |
| 2002/0087216 A1 | 7/2002 | Atkinson et al. |
| 2002/0116072 A1 | 8/2002 | Rubie et al. |
| 2002/0143408 A1 | 10/2002 | Townsend et al. |
| 2002/0183860 A1 | 12/2002 | Wilkinson |
| 2003/0093158 A1 | 5/2003 | Phillips |
| 2003/0120353 A1 | 6/2003 | Christensen |
| 2004/0064195 A1 | 4/2004 | Herr |
| 2004/0068327 A1 | 4/2004 | Christensen |
| 2004/0122529 A1 | 6/2004 | Townsend et al. |
| 2004/0181289 A1 | 9/2004 | Bedard |
| 2005/0038525 A1 | 2/2005 | Doddroe et al. |
| 2005/0107889 A1 | 5/2005 | Bedard et al. |
| 2005/0137717 A1 | 6/2005 | Gramnäs et al. |
| 2005/0267603 A1 | 12/2005 | Lecomte et al. |
| 2006/0069450 A1 | 3/2006 | McCarvill et al. |
| 2007/0027557 A1 | 2/2007 | Jonsson |

FOREIGN PATENT DOCUMENTS

| | | | |
|---|---|---|---|
| DE | 299 12 832 U1 * | 11/2000 |
| EP | 0 940 129 A1 | 11/1992 |
| EP | 1 149 568 A1 | 10/2001 |
| FR | 2658717 | 8/1991 |
| GB | 117547 | 8/1918 |
| GB | 120462 | 11/1918 |
| GB | 621576 | 4/1949 |
| GB | 625528 | 6/1949 |
| GB | 1371996 | 10/1974 |
| KR | 2000-0000930 | 1/2000 |
| KR | 2000-0047310 | 7/2000 |
| KR | 2001-0055393 A * | 7/2001 |
| WO | WO 88/06431 | 9/1988 |
| WO | WO/9304645 | 3/1993 |
| WO | WO 94/18914 | 9/1994 |
| WO | WO 96/04869 A1 | 2/1996 |
| WO | WO 98/53769 | 12/1998 |
| WO | WO 99/52476 | 10/1999 |
| WO | WO 00/27317 | 5/2000 |
| WO | WO 01-06965 A1 | 2/2001 |
| WO | WO 02/02034 A1 | 1/2002 |
| WO | WO 02/051342 | 7/2002 |
| WO | WO 2004/032809 | 4/2004 |
| WO | PCT/US2004/002554 | 8/2004 |
| WO | WO 2005/048887 | 6/2005 |

OTHER PUBLICATIONS

English translation of KR 2000-0002059 A.*
The Quantum Foot brochure, 10 pages total.*
Hosmer Dorrance Corporation: The Quantum Foot (4 pages).*
English translation of IPOS, DE 299 12 832 U1.*
Ohio Willow Wood Company: Carbon Copy System III brochure, 5 pages; circa 1990.*
English translation of KR 2000-0002059 A (Jan. 15, 2000).*
The Quantum Foot brochure, 10 pages total; circa 1988.*
Hosmer Dorrance Corporation, The Quantum Foot (4 pages): circa 1988.*
English translation of IPOS, DE 299 12 832 U1 (Nov. 23, 2000).*
Commercial Ad for College Park Venture Prosthetic Foot; http://www.college-park.com/assets/pdf/VentureInfoSheets.pdf, © 2003, and www.college-park.com/CPStore/ProductInfoVenture.asp; available before Aug. 15, 2003, (4 pages).
Freedom Innovations FS2000 LP product; http://www.freedom-innovations.com/html/details.html, © 2003; available before Aug. 15, 2003, (one page).
Össur Allurion product; http://www.ossur.com/template1.asp?pageid=84 and product catalog pp. 146-149; available before Aug. 15, 2003, (5 pages).
Össur Elation product; http://www.ossur.com/template1.asp?pageid=263 and product catalog pp. 193-196; available before Aug. 15, 2003, (6 pages).
U.S. Appl. No. 11/537,227, filed Sep. 29, 2006, Orn Jonsson.
U.S. Appl. No. 10/742,455, filed Dec. 18, 2003, Gramnäs et al.
U.S. Appl. No. 10/987,940, filed Nov. 12, 2007, Lecomte, et al.
English Translation Bernhardsson, SE 9400380-3A, published on Aug. 5, 1995.
International Search Report dated Apr. 28, 2006 for PCT/US2005/017884 filed May 20, 2005.
Office Action Apr. 8, 2008 in U.S. Appl. No. 10/987,940.
Non-final Office Action mailed Oct. 5, 2006 in U.S. Appl. No. 10/742,455.
Final Office Action mailed Mar. 27, 2007 in U.S. Appl. No. 10/742,455.
Final Office Action mailed Oct. 12, 2007 in U.S. Appl. No. 10/742,455.
Non-final Office Action mailed Apr. 3, 2008 in U.S. Appl. No. 10/742,455.
Final Office Action mailed on Feb. 4, 2010 in U.S. Appl. No. 10/742,455.
Non-final Office Action mailed on Sep. 2, 2010 in U.S. Appl. No. 11/537,227.

Chinese Office Action dated Jul. 10, 2009 in Application No. 200480023422.5, filed Aug. 6, 2004.

Freedom Innovations Runway product; http://www.freedom-innovations.com/product_details.asp?seriesid=2&prodid=11, © 2004; available before Dec. 18, 2003, 1 page.

ÖSSUR Total Concept product, ÖSSUR Products Catalog 2001-2002, pp. 243-249.

Otto Bock—Axtion product; http://www.ottobockus.com/products/lower_limb_prosthetics/axtion.asp; believed to have been released May 2004, 2 pages.

Non-final Office Action mailed on Aug. 30, 2010 in U.S. Appl. No. 11/537,227.

* cited by examiner

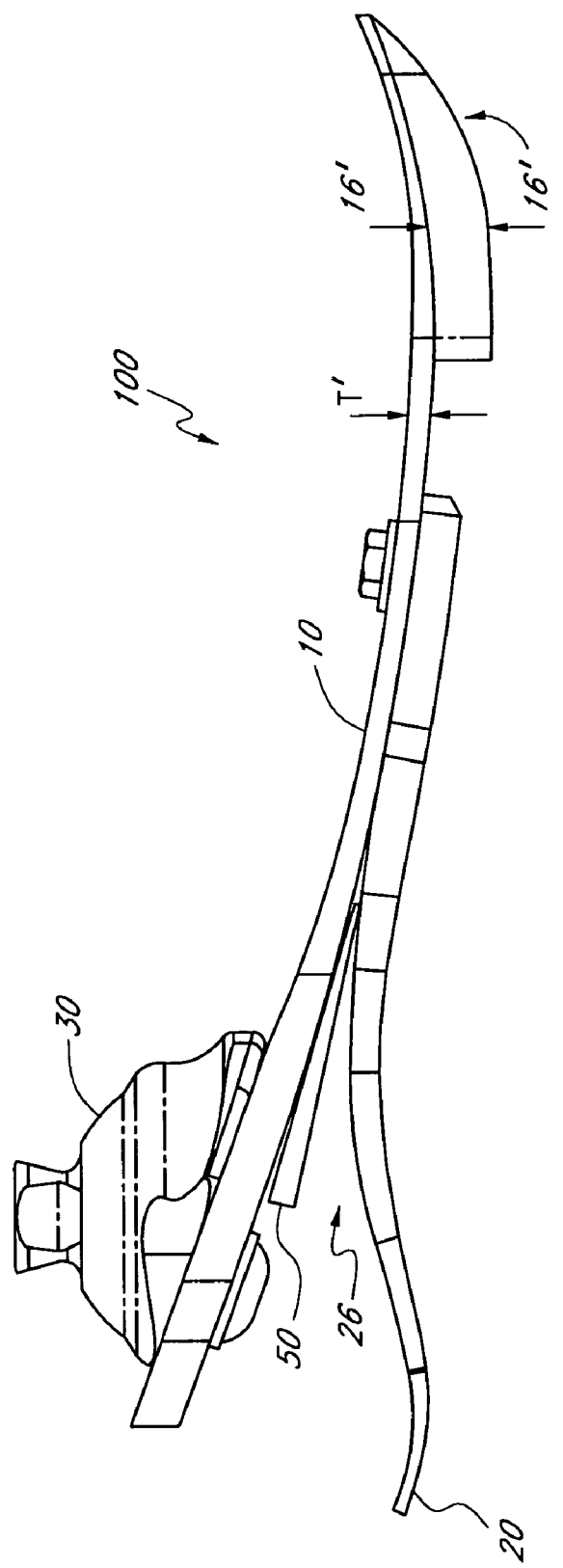

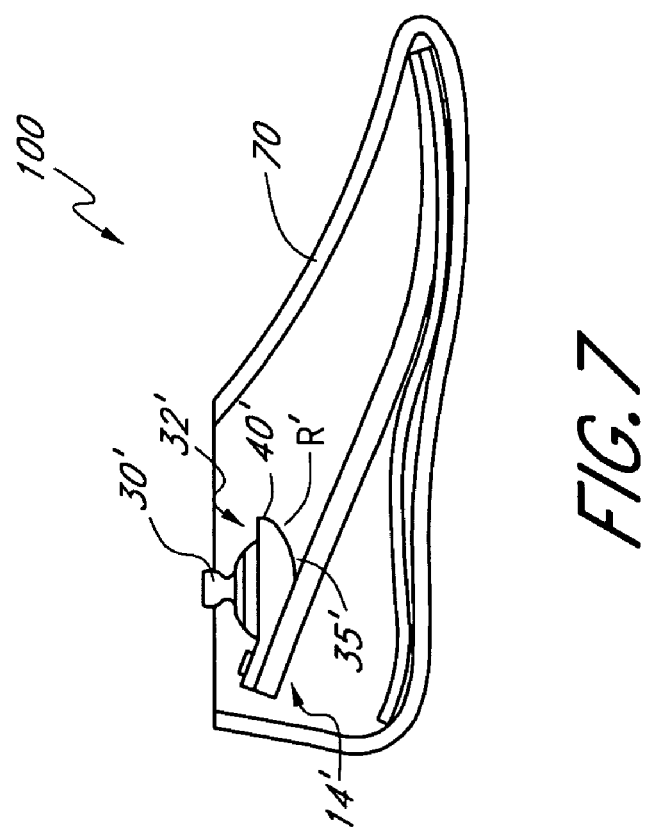

LOW PROFILE PROSTHETIC FOOT

BACKGROUND OF THE INVENTION

1. Field of the Invention

Embodiments of the present invention relate to lower limb prostheses in general, and, in one embodiment, to a prosthetic foot having an adapter connected to a foot member, the adapter configured to provide improved foot member flexion.

2. Description of the Related Art

Prosthetic feet of different designs are well known in the art. The various conventional designs have sought to solve various limitations associated with prosthetic feet.

Some conventional designs attempt to provide the feel and fluid range of motion of a human foot's natural stride. One approach is to incorporate springs to store and release energy during motion of the prosthetic foot. Such springs can be of different shapes, such as C-shaped or U-shaped. However, such foot designs tend to be bulky and may be difficult to wholly contain in a cosmesis. Additionally, in some instances the efficiency of the springs may deteriorate following prolonged use, resulting in less efficient energy storage and release during motion of the foot.

Other conventional designs attempt to provide the flexibility and stability of a human foot. One approach is to provide a foot member that is split along at least a portion of its length. The split foot member is thus composed of individual "toes" that are capable of flexing substantially independently of each other. This provides a prosthetic foot with increased stability. However, a split-toe foot alone may not provide the desired fluid range of motion of a human foot's natural stride.

Still other designs attempt to provide a strong and resilient prosthetic foot capable of accommodating a wide a range of activity levels, such as walking, running, and jumping, by focusing on the strength of the prosthetic foot. Accordingly, various materials have been used in the manufacture of prostheses to provide the desired strength as well as weight. However, many prosthetic foot designs are limited to a certain impact level and are designed for users in a certain weight range.

Yet other designs are directed to particular amputees. For example, Symes prosthetic foot designs are directed to amputees with long residual limbs. However, conventional foot designs are generally not designed to be used by both amputees with long residual limbs and those with shorter residual limbs, such as above-knee amputees.

Many prosthetic foot designs are enclosed in a cosmesis to improve its aesthetics. However, many designs are difficult to maintain when enclosed in said cosmesis. For example, the location of the ankle component or pyramid on some designs makes it difficult to remove the prosthetic foot from the cosmesis or to access the bolts connecting the ankle or pyramid to the prosthetic foot.

Thus, there is a need for an improved prosthetic foot that provides the desired strength, stability, fluidity of motion, and flexibility of use.

SUMMARY OF THE INVENTION

In at least one embodiment, a prosthetic foot is configured to provide a more fluid heel-to-toe movement during foot motion. Additionally, the prosthetic foot advantageously provides a low-profile foot for use by amputees with long residual limbs, as well as by amputees with shorter residual limbs. In at least some embodiments, the prosthetic foot further provides increased strength and resilience.

In one embodiment, an improved adapter is provided for attachment to a pylon or other leg prosthesis. The adapter is preferably mounted at a posterior section thereof to a posterior portion of a foot member, or other elongate support member, and includes an anterior portion configured to move relative to the foot member. In one preferred embodiment, the adapter is mounted in approximately the posterior 25% of the foot member, making the foot easier to remove from a cosmesis, facilitating access to the adapter and, for example, the bolts that connect it to the foot member. The foot member is preferably curved and optimized to flex.

The adapter preferably has a base or lower surface that slopes at an angle corresponding generally to the angle of the rear section of the foot member relative to a support surface. For example, where the adapter includes a pyramid, this angle is such that the pyramid is aligned generally vertically relative to the support surface when the adapter is attached to the foot member. Additionally, in one embodiment, the adapter is secured to the foot member such that the anterior section of the adapter is thus advantageously allowed to move toward, or "roll-up" onto the foot member during foot motion. For example, the adapter is secured to the foot member in cantilever fashion, connected solely at its posterior section. In one embodiment, the lower surface of the adapter includes a curved portion or edge defined by a radius of curvature proximal the anterior section of the adapter. Said radius of curvature can be varied to provide the desired degree of "roll-up" during motion. Additionally, the adapter advantageously can comprise a variety of structures, such as a socket, a pyramid, and a tube clamp connector.

In another embodiment, the prosthetic foot further comprises a heel member mounted to the foot member intermediate an anterior portion and the posterior portion of the foot member and extending rearwardly therefrom. The heel member and foot member preferably define a longitudinal slot therebetween configured to receive a resilient wedge member. The wedge member is configured to alter the stiffness characteristics of the heel member and influence the fluidity of the heel to toe loading.

In still another embodiment, the foot member and heel member can each be split into at least two independent members capable of flexing substantially independently of each other and substantially completely about their lengths during motion. This advantageously provides the prosthetic foot with increased stability.

In at least one embodiment, the prosthetic foot has improved strength and resiliency. For example, in one preferred embodiment, the prosthetic foot is rated for use in all impact levels. Additionally, the prosthetic foot can be used by amputees with weights varying over a wide range.

In one embodiment, the prosthetic foot is a low profile prosthetic foot. The low profile foot comprises a foot member with a length extending between a front end and a rear end of the foot member, and anterior and posterior portions. The posterior portion is inclined at an angle relative to the anterior portion and relative to a support surface. The foot member also has multiple toe members configured to flex substantially independently of one another at least partially along their length, said toe members defined by one or more longitudinal slots extending through said foot member from the front end and rearwardly therefrom.

The low profile prosthetic foot also comprises a heel member with a length extending from a front end to a rear end thereof, a generally flat anterior portion, and a curved posterior portion. The anterior portion is secured to the foot member intermediate the front and rear ends of the foot member so as to define a longitudinal slot between the foot member and the heel member. The heel member also has multiple heel sections configured to flex substantially independently of one another at least partially along their length, said heel sections defined by one or more longitudinal slots extending through said heel member from its rear end and forwardly therefrom.

Additionally, the low profile foot also comprises an adapter with anterior and posterior sections and a base, wherein the adapter is connected solely at its posterior section to the foot member. The anterior section is configured to move relative to the foot member. Additionally, the base is inclined relative to the support surface at an angle generally equal to the angle of the posterior portion of the foot member relative to the support surface. At least a portion of the base is configured to contact the posterior portion of the foot member. The base defines an edge having a radius of curvature at the anterior section, wherein the anterior section is configured to roll-up along said edge onto the foot member.

In another embodiment, the prosthetic foot is a low profile prosthetic foot comprising a foot member that extends between a front end and a rear end thereof and has an anterior and posterior portions, wherein the posterior portion is inclined at an angle relative to the anterior portion and a support surface. The low profile prosthetic foot also comprises a heel member that connects to the foot member at a point intermediate the front and rear ends of the foot member and extends rearwardly therefrom. Further, the low profile prosthetic foot comprises an adapter with anterior and posterior sections and a base, wherein the adapter connects at its posterior section to the posterior portion of the foot member. The anterior section is adapted to move relative to the foot member. The base of the heel member is also inclined at an angle relative to the support surface, wherein at least a portion of the base is configured to contact the posterior portion of the foot member. The base also defines an edge having a radius of curvature at the anterior section, wherein the anterior section is configured to roll-up along said edge onto the foot member.

In still another embodiment, the prosthetic foot is a low profile prosthetic foot comprising a foot support that extends between a front end and a rear end and has anterior and posterior portions, wherein the posterior portion is inclined at an angle relative to a support surface. The low profile prosthetic foot also comprises a heel support connected to the foot support. Additionally, the prosthetic foot comprises an adapter with anterior and posterior sections and a base, wherein the base is inclined at an angle relative to the support surface. The adapter is mounted to the posterior portion of the foot support. At least a portion of the base is configured to contact the posterior portion of the foot support, while the anterior section is configured to move relative to the foot support.

In yet another embodiment, an adapter is provided for use in connecting a prosthetic foot to a socket, intermediate prosthesis, such as a pylon, or the like. The adapter comprises a pyramid provided at an upper portion of the adapter, wherein the pyramid defines an axis that extends generally vertically through said pyramid relative to a support surface. The adapter also comprises a base provided at a lower portion of the adapter that extends along a length of the adapter. The base has an inclined surface that inclines upward from an anterior section to a posterior section of the adapter relative to a support surface. The base along the anterior section has a roll-up surface adapted to allow relative motion between the adapter and the prosthetic foot when the adapter is connected to the prosthetic foot.

BRIEF DESCRIPTION OF THE DRAWINGS

FIG. 6A is a side view of another embodiment of a prosthetic foot comprising a resilient wedge.

FIG. 7 is a side view of another embodiment of a prosthetic foot including a different adapter.

DETAILED DESCRIPTION OF THE PREFERRED EMBODIMENTS

Figure 1:
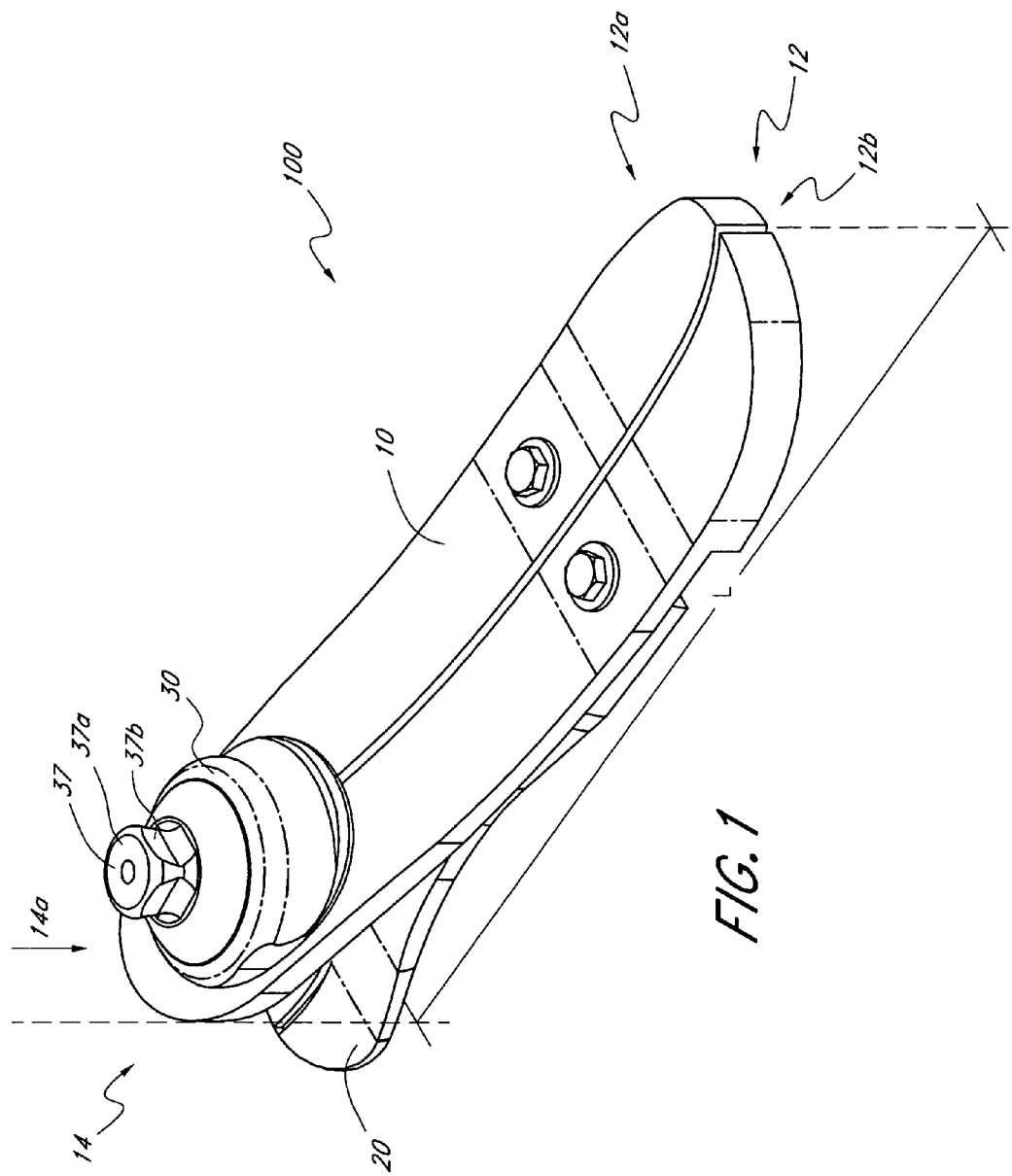
FIG. 1 is a top perspective view of a prosthetic foot in accordance with one embodiment of the invention.
Figure 2:
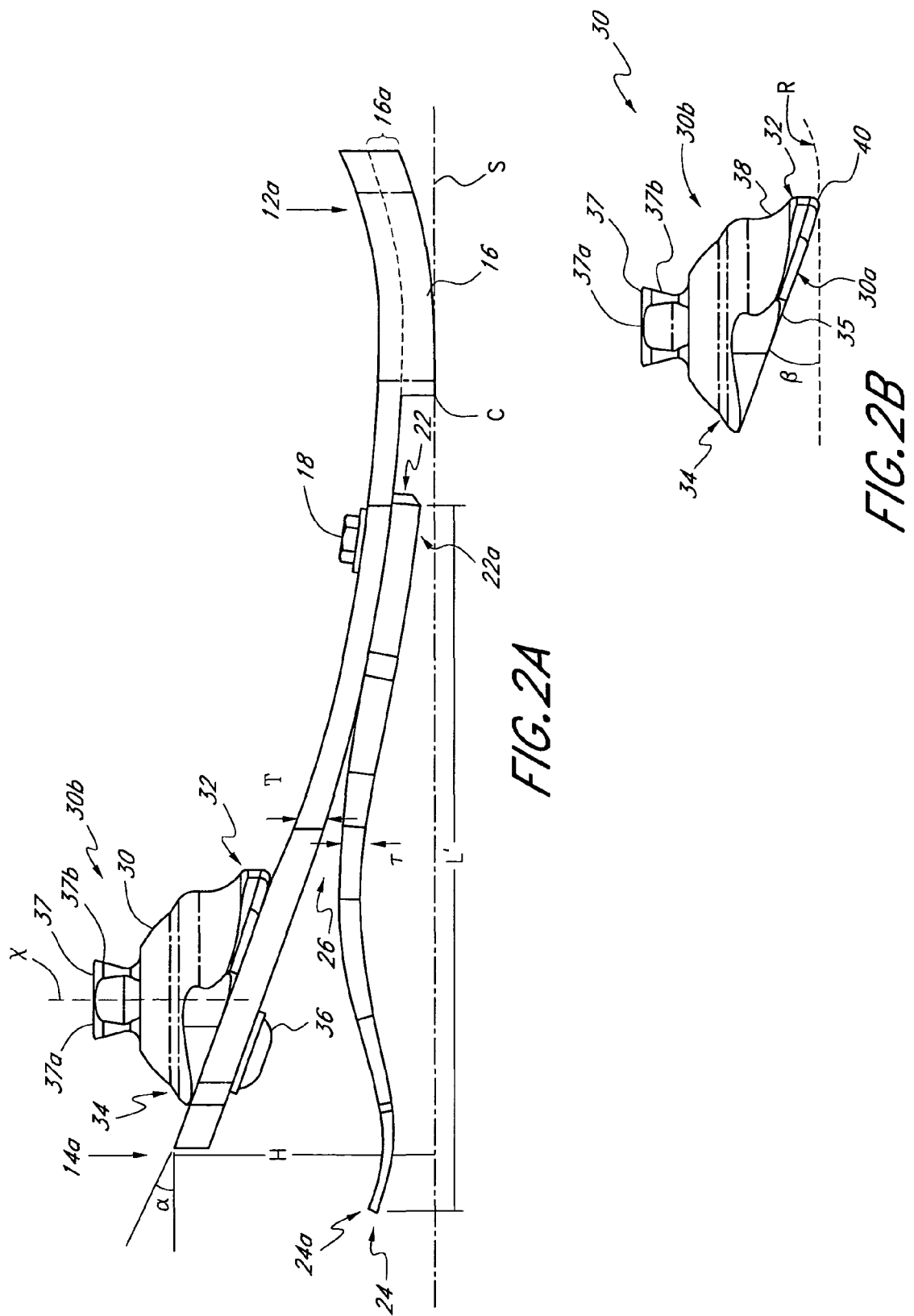
FIG. 2A is a side view of the prosthetic foot embodiment illustrated in FIG. 1.
FIG. 2B is an enlarged view of the adapter illustrated in FIG. 2A.

FIGS. 1-2A illustrate one embodiment of a prosthetic foot 100. Preferably, the prosthetic foot 100 comprises a foot member or support 10 which may have an elongate configuration having a length L extending between a front end 12 and a rear end 14. As used herein, length L refers to the horizontal length of the foot member 10 along a plane parallel to a support surface S on which the prosthetic foot 100 rests. In one embodiment, the length L may be between about 18 and 30 cm, corresponding to the specific size of the prosthetic foot 100. In one preferred embodiment, the length L is about 23 cm. The ends 12, 14 of the foot member 10 preferably have rounded or curved edges. The foot member 10 preferably also comprises an anterior portion 12a and a posterior portion 14a, wherein the anterior portion 12a can include a front toe portion 12b. In one preferred embodiment, the foot member 10 can be generally shaped like the sole of a human foot and the length L be approximately equal to that of a natural human foot. Alternatively, the foot member 10 may be shorter. In addition, the foot member 10 may comprise multiple pieces separated, for example, transversely or longitudinally from each other. In another embodiment, the foot member 10 may be an integral piece, may be substantially flat, and have a substantially rectangular traverse cross-section along its length L.

As shown in FIG. 1, the foot 100 further comprises a heel member 20, which may have an elongate configuration extending rearwardly from a location on the foot member 10 intermediate the front end 12 and rear end 14. Optionally, the heel member 20 can extend beyond the rear end 14 of the foot member 10. Like the foot member 10, heel member 20 may be substantially flat and have a substantially rectangular traverse cross-section along its length. Although the heel member 20 is depicted as only extending from an intermediate location between the front end 12 and rear end 14 of the foot member 10, it will be appreciated that the heel member 20 may be part of a foot member that extends substantially from heel-to-toe. Like the foot member 10, the heel member 20 (or any foot member that it may be a part of) need not be one integral piece, and can comprise multiple pieces separated, for example, transversely or longitudinally from one another. It will also be appreciated that the heel member 20 need not be an elongate member, and can have other configurations to provide heel support. In some embodiments, a separate heel member 20 may not even be necessary.

The prosthetic foot 100 also comprises an adapter 30 mounted to the foot member 10 near the rear end 14 of the foot member 10. Features of the adapter 30 will be discussed further below.

FIG. 2A shows a side view of the prosthetic foot 100 illustrated in FIG. 1. Preferably, the anterior portion 12a of the foot member 10 is generally planar and extends generally parallel or horizontal relative to the support surface S. The posterior portion 14a is generally inclined with respect to the anterior portion 12a and the support surface S. For example, the posterior portion 14a of the foot member 10 can extend at an angle α relative to the support surface S. In one preferred embodiment, the angle α can be between about 10 and 45 degrees. More preferably, the angle α can be about 20 degrees. Said inclined posterior portion 14a defines a heel height H from the support surface S to the rear end 14. In one preferred embodiment, the heel height H can be between about 40 and 70 mm. More preferably, the heel height H can be about 60 mm or less.

In one preferred embodiment, the foot member 10 of FIG. 2A may extend at a constant slope (i.e., linearly) between the anterior portion 12a and the posterior portion 14a of the foot member 10. In another preferred embodiment, said foot member 10 may extend in a gradual and continuous upward curve between the anterior portion 12a and the posterior portion 14a. For example, the foot member 10 may extend at a gradually increasing slope between the anterior and posterior portions 12a, 14a. In still another preferred embodiment, the incline between the anterior portion 12a and posterior portion 14a may comprise a combination of constant and gradually increasing slopes. For example, the foot member 10 may initially extend from the anterior portion 12a at a gradually increasing slope and transition to a constant slope. Similarly, the foot member may initially extend from the anterior portion 12a at a constant slope and transition to a gradually increasing slope.

The foot member 10, as shown in FIG. 2A, is preferably made of a material adapted to flex during motion from heel-strike through toe-off and having the desired strength. In one preferred embodiment, the foot member 10 can be fabricated using a carbon filament with, for example, an epoxy binder. However, other filament types can be used, such as glass, Kevlar, and nylon, to ensure lightweight and structural and dynamic characteristics consistent with the amputee. Preferably, the foot member 10 is constructed using a combination of longitudinal (lengthwise) filaments interspersed with a fraction of transverse filament to bind the longitudinal filaments together and prevent the separation thereof under load. In one embodiment, longitudinal or 90-degree filament and transverse or 0-degree filament can be used. However other filament arrangements can be used. For example, longitudinal and transverse filaments can be arranged at a variety of angles relative to each other, such as 45 degrees. Preferably, the longitudinal filaments are arranged in laminae that are located in immediate contact with one another. For example, the laminae can be superimposed on each other, maintained in operative relationship by an encapsulating polymer, and be susceptible to a bending stress determined by the thickness of the laminae. The number of laminae preferably varies with the size of the prosthetic foot 100. For example, the foot member 10 of a smaller prosthetic foot 100 can comprise a lower number of laminae than the foot member 10 of a larger prosthetic foot 100. Accordingly, a thickness T of the foot member 10 will vary with the number of laminae used to fabricated the foot 100. Further details of materials suitable for use in fabricating the foot member 10 can be found in U.S. Pat. Nos. 4,547,913 and 4,822,363, both of which are hereby incorporated by reference.

The foot member 10 in FIG. 2A can be fabricated using, for example, injection molding and/or the use of thermoplastic materials and processes, or any of a range of combinations thereof. In one preferred embodiment, chopped fiber may be blended in a thermoplastic or thermoset resin and the resulting mixture injection molded into an appropriate configuration. In another preferred embodiment, thermoplastic laminae may be alternatively or additionally wound around an injection-molded core, or a thermoplastic resin may be injected between thermoplastic or thermoset laminae, whereby the laminates are bonded onto the injected material.

In one preferred embodiment, as shown in FIG. 2A, a crepe portion 16 is attached to the underside of the anterior portion 12a of the foot member 10 and is aligned with the anterior portion 12a of the foot member 10 so as to not extend past the anterior portion 12a. Preferably, the crepe portion 16 comprises a resilient pad or cushion. For example, the crepe portion 16 can be made of a compressible material. The crepe portion 16 can also be made of a porous material. In one embodiment, the crepe portion 16 can be made of solid urethane. In one preferred embodiment, the crepe portion 16 is attached to the anterior portion 12a of the foot member 10 with an adhesive. However, other attachment means can be used, such as bolts, screws, and bands wrapped around the crepe portion 16 and the foot member 10. The crepe portion 16 is preferably configured to have a shape corresponding to the shape of the foot member 10. For example, the crepe portion 16 can have a rounded edge corresponding to the rounded edge of the front end 12. In the illustrated embodiment, the crepe portion 16 has a uniform thickness 16a. In another preferred embodiment, the crepe portion 16 can have a varying thickness (see FIG. 6A). For example, the crepe portion 16 can have a decreasing thickness 16a' in the direction of the front end 12 of the foot member 10. In other preferred embodiments, the foot member 10 does not have a crepe portion 16 attached to it, so that the anterior portion 12a of the foot member 10 operatively contacts the support surface S.

In the embodiment illustrated in FIG. 2A, the thickness T of the foot member 10 is generally uniform from the rear end 14 to the front end 12. Preferably, the thickness T is between about 2.5 and 15 mm. More preferably, the thickness T is about 7 mm. In another preferred embodiment (see FIG. 6), the foot member 10 has a varying thickness T' between the front end 12 and rear end 14. For example, the thickness T' can decrease from the posterior portion 14a to the anterior portion 12a of the foot member 10. In one preferred embodiment, the thickness T' can vary from between about 7 and 10 mm at the rear end 14 to between about 2.5 and 5 mm at the front end 12. More preferably, the thickness T' varies between about 8 mm at the rear end 14 to about 3 mm at the front end 12. Additionally, in one preferred embodiment, the thickness T' can vary in a manner similar to the thickness 16a' of the crepe portion 16. For example, as shown in FIG. 6, both the thickness T' of the foot member 10 and the thickness 16a' of the crepe portion 16 can decrease toward the front end 12 of the member 10. In another embodiment (not shown), the thicknesses T', 16a' can vary in opposite directions. For example, the thickness T' can decrease toward the front end 12 of the foot member 10, whereas the thickness 16a can increase toward the front end 12. One of ordinary skill in the art will recognize that the values given above will vary with the corresponding size and lay-up of the prosthetic foot, as discussed above.

As best seen in FIG. 2A, in one embodiment, the heel member 20 has a length L' extending between a front end 22 and rear end 24 and is removably connected to the foot member 10 at a location intermediate the front and rear ends 12, 14 of the foot member 10. Preferably, the heel member 20 is connected to the foot member 10 via at least one connector 18. In the illustrated embodiment, the connector 18 comprises two bolts that connect the foot member 10 to an anterior portion 22a of the heel member 20. However, the connector 18 can comprise other structures, such as rivets, welds, screws, and adhesives. Additionally, the connector 18 can also comprise a resilient band wrapped around the foot member 10 and heel member 20. In another preferred embodiment, the heel member 20 can be integrally formed with the foot member 10. Preferably, the heel member 20 has a substantially rectangular traverse cross-section along its length L'.

As shown in FIG. 2A, the heel member 20 extends from the connection point rearwardly toward a posterior portion 24a of the heel member 20. In the illustrated embodiment, the heel member 20 includes a curved lengthwise contour, wherein the anterior portion 22a is generally flat and the posterior portion 24a is generally curved. For example, the posterior portion 24a can have a generally S-shaped curve. In the illustrated embodiment, the heel member 20 has a thickness τ that varies from a minimum at the posterior portion 24a to a maximum at the anterior portion 22a. Preferably, the thickness τ varies between about 2.5 and 5 mm at the posterior portion 24a to between about 5 and 10 mm at the anterior portion 22a. More preferably, the thickness τ varies between a minimum of about 3 mm at the posterior portion 24a to a maximum of about 7 mm at the anterior portion 22a. In another preferred embodiment (not shown), the thickness τ' can be uniform between the posterior portion 24a and the anterior portion 22a. In still another preferred embodiment (not shown), the maximum thickness τ can be generally equal to the maximum thickness 16a of the crepe portion 16 so that the anterior portion 22a of the heel member 20 and the crepe portion 16 provide a generally uniform contact surface C adapted to contact the support surface S. One of ordinary skill in the art will recognize that the values given above will vary with the corresponding size and lay-up of the prosthetic foot, as discussed above.

Figure 3:
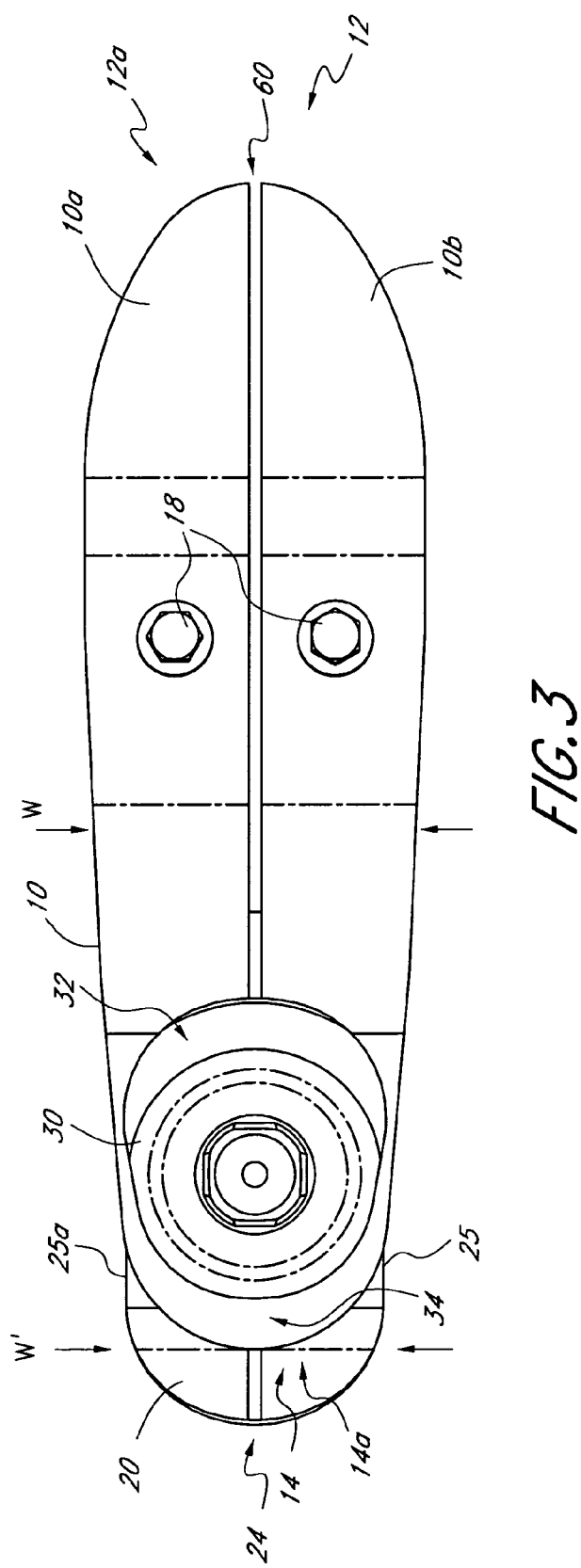
FIG. 3 is a top view of the prosthetic foot embodiment illustrated in FIG. 1.
Figure 5:
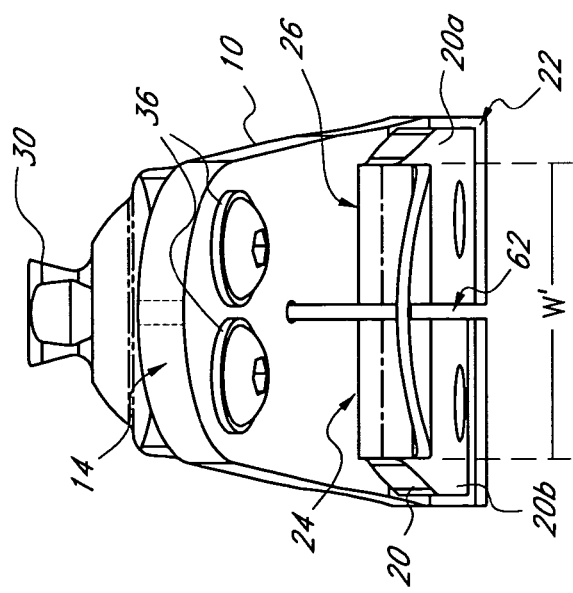
FIG. 5 is a rear elevational view of the prosthetic foot embodiment illustrated in FIG. 1.

As illustrated in FIGS. 1, 3 and 5, the heel member 20 can also have curved widthwise contour. For example, the heel member 20 can have a rounded or curved rear end 24 and a width W' that varies from a minimum width at the rear end 24 to a maximum width at the front end 22. Preferably, the width W' varies between about 30 and 50 mm at the posterior portion 24a and between about 55 and 75 mm at the anterior portion 22a. In the illustrated embodiment, the width W' varies between about 65 mm at the anterior portion 22a and about 50 mm at the posterior portion 24a. In one embodiment, the width W' can be defined by an edge 25 that gradually and continuously curves between the rear end 24 and the front end 22. In another embodiment, the edge 25 can have a linear section 25a proximal the rear end 24 and a curved section 25b proximal the front end 22, so that the width W' includes a constant section and a gradually increasing section. Preferably, the heel member 20 extends rearwardly from the foot member 10 so as to define a longitudinal slot 26 between the heel member 20 and the foot member 10. The heel member 20 can be fabricated in the same manner and from the same materials discussed above with regard to the foot member 10.

Additionally, in one preferred embodiment (not shown), a crepe portion can be attached to the posterior portion 24a of the heel member 20 so as to contact the support surface S.

As best shown in FIG. 2A, the adapter 30 defines an anterior section 32 and a posterior section 34 and has a major axis X. Additionally, the adapter 30 preferably defines a base 35 at a lower portion 30a thereof extending from the posterior section 34 to the anterior section 32, as shown in FIG. 2B. The base 35 is preferably between about 50 and 65 mm in length. In the illustrated embodiment, the base is about 55 mm long. The base 35 is generally inclined relative to the support surface S at an angle β. Preferably, the angle β is generally equal to the angle α of the posterior portion 14a relative to the support surface S. Also, in one embodiment, the incline of the base 35 generally conforms to the incline of the foot member 10. For example, if the foot member 10 has a constant slope, as previously discussed, the base 35 of the adapter 30 also preferably has said constant slope. The adapter 30 is preferably removably connected to the posterior portion 14a of the foot member 10 via at least one adapter connector 36. Preferably, the adapter connector 36 connects the foot member 10 only to the posterior section 34 of the adapter 30. In the illustrated embodiment, the adapter connector 36 comprises two bolts (see also FIG. 5). However, the adapter connector 36 can comprise other structures, such as screws, rivets, welds, adhesives, and bands wrapped around the adapter 30 and the foot member 10. Additionally, in one embodiment, the adapter 30 may be permanently attached to the posterior portion 14a of the foot member 10 via, for example, an adhesive, a resin, or the like. Accordingly, in a preferred embodiment, the posterior section 34 of the adapter 30 is maintained in a fixed position relative to the foot member 10 while the anterior section 32 of the adapter 30 is allowed to move relative to the foot member 10 when the foot member 10 flexes. Further details are described below.

As shown in FIGS. 1-2B, one embodiment of the adapter 30 comprises a pyramid 37 at an upper portion 30b thereof adapted to connect to a pylon or other prosthesis (not shown). The pyramid 37 has a generally flat top surface 37a and at least one side surface 37b. In the illustrated embodiment, the side surface 37b comprises four generally flat faces inclined relative to the axis X. However, in other embodiments, the side surface 37b can comprise a cylindrical surface or may extend generally parallel to the axis X.

Optionally, the adapter 30, as shown in FIGS. 2A-2B, may define a recessed surface 38 configured to reduce the weight of the adapter 30. In the illustrated embodiment, the recessed surface 38 is a groove formed on the anterior section 32 and extending partially around the circumference of the adapter 30. However, the recessed surface 38 can have other shapes, such as a circumferentially extending channel. Additionally, other means can be used to reduce the weight of the adapter 30, such as drilling holes, slots or the like.

Continuing with FIG. 2A, the adapter 30 is preferably mounted to the foot member 10 so that it is positioned between about the posterior 20% to 33% of the foot member 10. More preferably, in one embodiment, the adapter 30 is mounted so that it is positioned in approximately the posterior 25% of the foot member 10. For example, where the length L of the foot member 10 is about twelve inches, the adapter is preferably mounted in the posterior three inches of the foot member 10.

As shown in FIG. 2B, the base 35 defines an edge 40 at the anterior section 32 of the adapter 30 and is configured to roll-up onto the foot member 10. For example, in the illustrated embodiment, the edge 40 curves at a radius R relative to the base 35 such that the adapter 30 rolls-up onto the foot member 10 during motion of the foot 100, as described below. The radius of curvature R is preferably between about 0.5 and 4 cm. In the illustrated embodiment, the radius of curvature R is about 1 cm. However, the edge 40 need not be curved or have a radius R for the adapter to roll-up onto the foot member 10. In another embodiment (not shown), the base 35 of the adapter may be substantially flat and extend from the posterior section 34 to the anterior section 32 so as to define a longitudinal gap between the base 35 and the foot member 10. Accordingly, during motion of the foot 100, the anterior portion 32 can move relative to, or roll-up onto, the foot member 10. In another embodiment (not shown), the base 35 can comprise a flat portion and a curved portion. For example, the base 35 can have a generally flat portion at the posterior section 34 and a generally curved portion at the anterior section 32. In another embodiment (not shown), the base 35 can have a generally curved portion at the posterior end 34 and a generally flat portion at the anterior section 32. In still another embodiment (not shown), the base 35 can comprise multiple generally flat portions, or ledges, each inclined at a different angle relative to the support surface S.

The adapter 30 shown in FIGS. 1-5 is preferably made of metal or metal alloys with suitable strength and stiffness characteristics corresponding to the anticipated load on the prosthetic foot 100. In embodiments of the prosthetic foot 100 exposed to lower or moderate loads, the adapter 30 can be made of aluminum, stainless steel, or the like. In embodiments of the prosthetic foot 100 exposed to large loads, the adapter 30 can be made of metals such as titanium.

FIG. 6A shows one embodiment of the prosthetic foot 100 comprising at least one resilient wedge 50. The at least one wedge 50 is preferably removably disposed in the slot 26 between the foot member 10 and the heel member 20. Optionally, a plurality of wedges 50 can be disposed in the slot 26. In another preferred embodiment, the at least one wedge 50 can be fixed in the slot 26 via, for example, an adhesive. Various other means can be used to fix the wedge 50 in the slot 26. For example, the wedge 50 can be bolted or screwed to the heel member 20 and/or the foot member 10. The at least one wedge 50 is preferably configured to provide additional shock absorption to the prosthetic foot 100. In one embodiment, the wedge 50 can be made, for example, of a hard plastic, such as polyurethane or polypropylene. The wedge 50 can also be made of a more compressible material, such as foam, natural or synthetic rubbers, or the like. However, the wedge 50 can be made of any material configured to provide adequate shock absorption to the prosthetic foot 100. A set of such wedges 50 can also be provided, wherein each wedge 50 has a different stiffness.

Figure 6B:
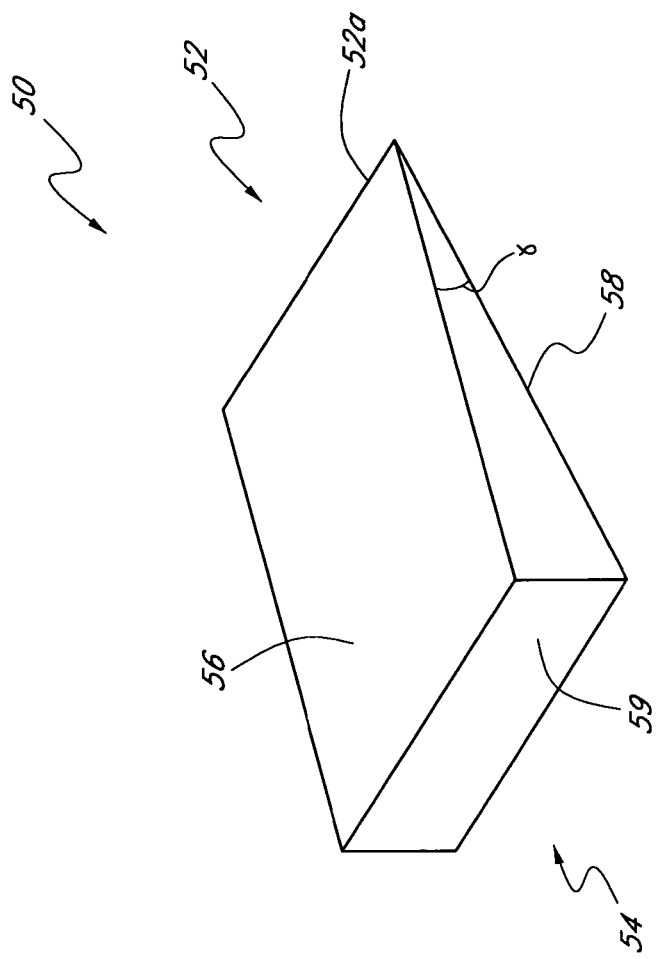
FIG. 6B is a profile view of the resilient wedge illustrated in FIG. 6.

As illustrated in FIG. 6B, the wedge 50 extends between a front end 52 and a rear end 54. In a preferred configuration, the wedge 50 has a generally triangular longitudinal cross-section, with a top surface 56 and a bottom surface 58 diverging at an angle γ from a common edge 52a at the front end 52 toward the rear end 54. A rear face 59 connects the top and bottom surfaces 56, 58 at the rear end 54. In the illustrated embodiment, the top and bottom surfaces 56, 58 can be generally planar. In another embodiment (not shown), the surfaces 56, 58 can be contoured to generally follow the corresponding contours of the foot member 10 and heel member 20. Preferably, the wedge 50 can be between about 40 and 60 mm long, between about 30 and 55 mm wide, and between about 2 and 10 mm tall. The wedge 50 also preferably has a durometer of between about 60A and 95A. More preferably, the wedge 50 has a durometer of about 85A. The angle γ preferably varies between about one and seven degrees. For example, in one embodiment, the wedge 50 can have an angle γ of about two degrees. In another embodiment, the wedge 50 can have an angle γ of about four degrees. In still another embodiment, the angle γ can be about six degrees. In another embodiment, the angle γ can be about eight degrees. In yet another embodiment, the angle γ can be about ten degrees.

FIG. 3 shows a top view of the prosthetic foot 100 illustrated in FIG. 1. In the illustrated embodiment, the posterior portion 14a of the foot member 10 is tapered relative to the anterior portion 12a of the foot member 10, so that the posterior portion 14a is less wide. For example, the foot member 10 can have a width W that tapers toward the rear end 14. In one preferred embodiment, the width W may taper gradually and continuously from the front end 12 of the foot member 10 to the rear end 14, such as in the form of a curve. In another preferred embodiment, the foot member 10 can have a generally constant width W along a portion of the length L and taper thereafter toward the rear end 14. In still another embodiment, the foot member 10 can have a generally constant width W from the front end 12 to the rear end 14.

As shown in FIG. 3, in at least one embodiment, the prosthetic foot 100 can have a foot member 10 that is split into multiple independent toe members configured to flex substantially independently of one another at least partially along their length. In the illustrated embodiment, the foot member 10 is split into two independent toe members 10a, 10b. For example, the foot member 10 may comprise at least one longitudinal slot 60 having a substantially constant width extending from the anterior portion 12a thereof towards a rear point proximal the posterior portion 14a of the foot member 10. In one embodiment, the slot 60 may extend underneath the location of the adapter 30 when it's connected to the foot member 10. In another embodiment, the slot 60 may extend partially along the foot member 10 to a location in front of the anterior section 32 of the adapter 30. In still other embodiments, the slot 60 may extend to a location proximal the anterior portion 12a of the foot member 10. In the illustrated embodiment, each connector 18 connects each of the independent toe members 10a, 10b to the heel member 20, as shown in FIG. 5.

Figure 4:
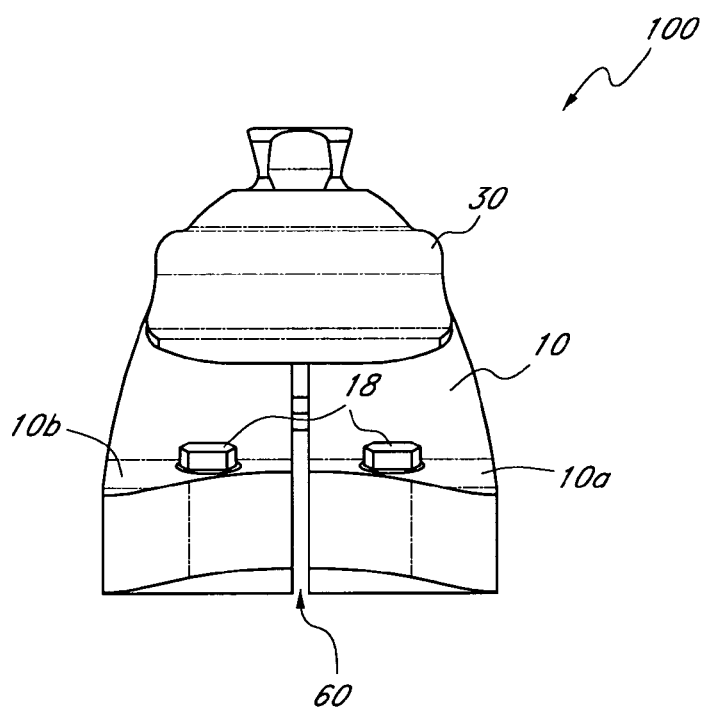
FIG. 4 is a front elevational view of the prosthetic foot embodiment illustrated in FIG. 1.

FIGS. 4-5 illustrate a front view and a rear view, respectively, of the prosthetic foot 100 shown in FIG. 1. As with the foot member 10, the heel member 20 can be split into multiple independent heel sections configured to flex substantially independently of one another at least partially along their length. In the illustrated embodiment, the heel member 20 is split into two independent heel sections 20a, 20b. For example, the heel member 20 may comprise at least one longitudinal slot 62 having a substantially constant width extending along the length L' of the heel member 20 from the front end 22 thereof to the rear end 24. In another embodiment, the slot 62 may extend partially along the heel member 20 from the front end 22 to a location near the rear end 24 of the heel member 20. In still other embodiments, the slot 62 may extend from the rear end 24 to a location proximal the front end 22 of the heel member 20. Preferably, the prosthetic foot 100 has as many independent toe members 10a, 10b as heel sections 20a, 20b. Each connector 18 thus connects one of the toe members 10a, 10b to a corresponding heel section 20a, 20b. Further details on split foot members and heel members can be found in U.S. Pat. Nos. 5,181,933 and 6,071,313, both of which are hereby incorporated by reference.

As illustrated in FIG. 5, the adapter connector 36 comprises two bolts removably connecting the posterior section 34 of the adapter 30 to the posterior portion 14a of the foot member 10. In the illustrated embodiment, the adapter 30 comprises a pyramid-style adapter for connection of a pylon or other prosthesis to the prosthetic foot 100. However, one of ordinary skill in the art will recognize that adapters of other types may be used with the embodiments of the present invention. For example, a socket, tube clamp or pylon having an inclined lower surface similar to the base 35 of the adapter 30 can be removably connected to the prosthetic foot 100. In a preferred embodiment, the axis X coincides with a longitudinal axis of the adapter used. For example, the axis X would coincide with the longitudinal axis of the pylon, socket, or tube clamp. Additionally, the axis X is preferably substantially vertical when the prosthetic foot 100 is at rest. As discussed above, the adapter 30, whether a pyramid, socket, tube clamp, pylon, or the like, can also be permanently attached to the foot member 10 via, for example, an adhesive, a resin, or the like.

FIG. 7 illustrates another embodiment of the prosthetic foot 100 with an adapter 30' removably connected to the posterior portion 14a of the foot member 10. In the illustrated embodiment, the adapter 30' defines an edge 40' at the anterior section 32' thereof having a radius R'. The radius R' is preferably smaller than the radius R of the prosthetic foot shown in FIG. 1, so that the curvature of the base 35' is more pronounced. The illustrated embodiment is thus configured to provide a greater roll-up effect of the adapter 30' onto the foot member 10 during motion of the prosthetic foot 100. The radius R' can be selectively varied to provide a desired roll-up effect. However, as discussed above with regard to the adapter 30, the base 35' need not be curved or have a radius R' for the adapter 30' to roll-up onto the foot member 10. As discussed above, the base 35' can be generally flat, generally curved, or a combination thereof and still be adapted to roll-up onto the foot member 10.

FIGS. 8-11 show another embodiment of a prosthetic foot 200. The prosthetic foot 200 has generally the same structure as the prosthetic foot 100 described above and is configured to operate in a similar manner. Accordingly, similar components are identified with the same reference numeral, followed by a "'''".

Figure 8:
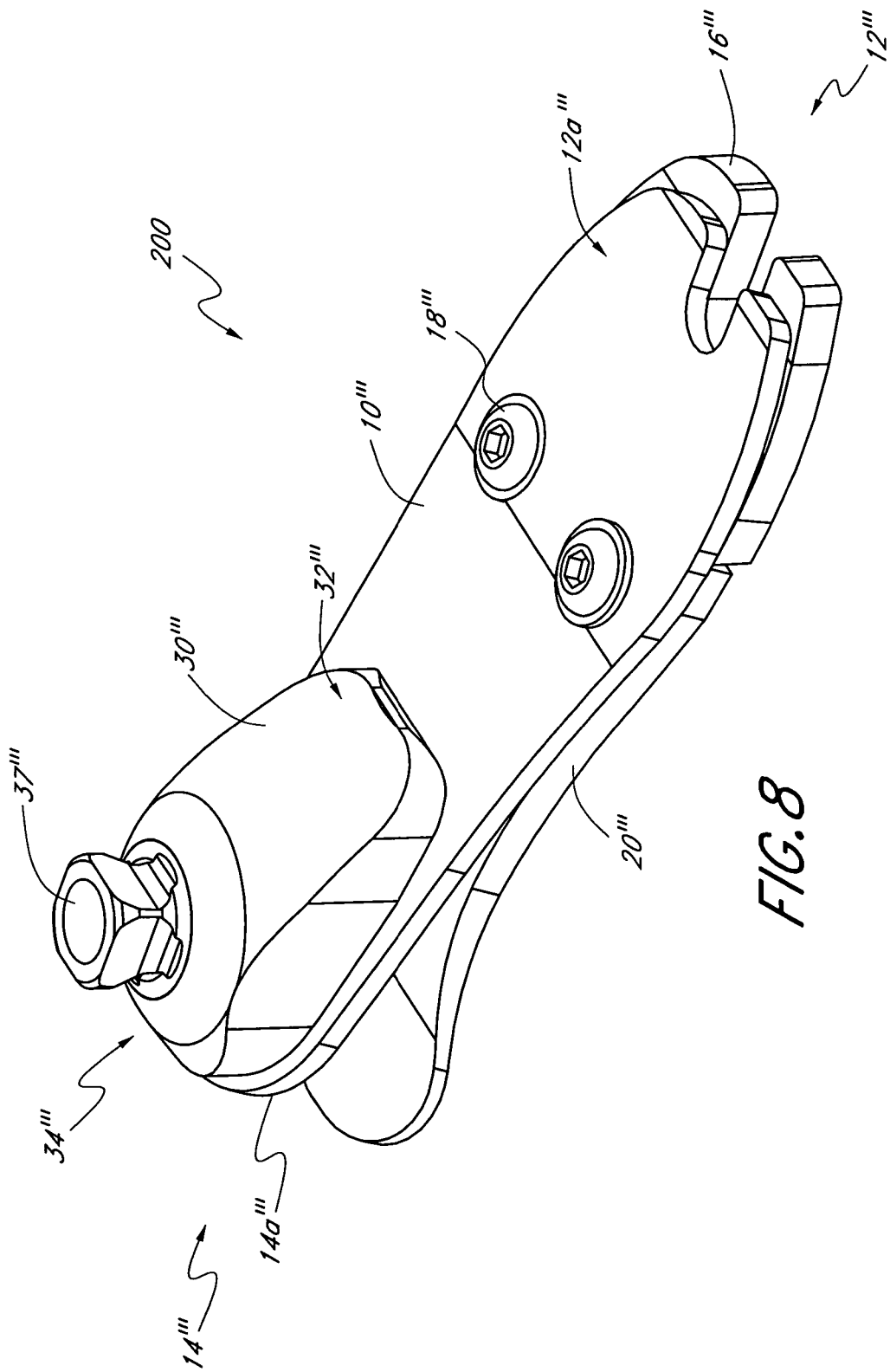
FIG. 8 is a top perspective view of a prosthetic foot in accordance with another embodiment of the invention.
Figure 9:
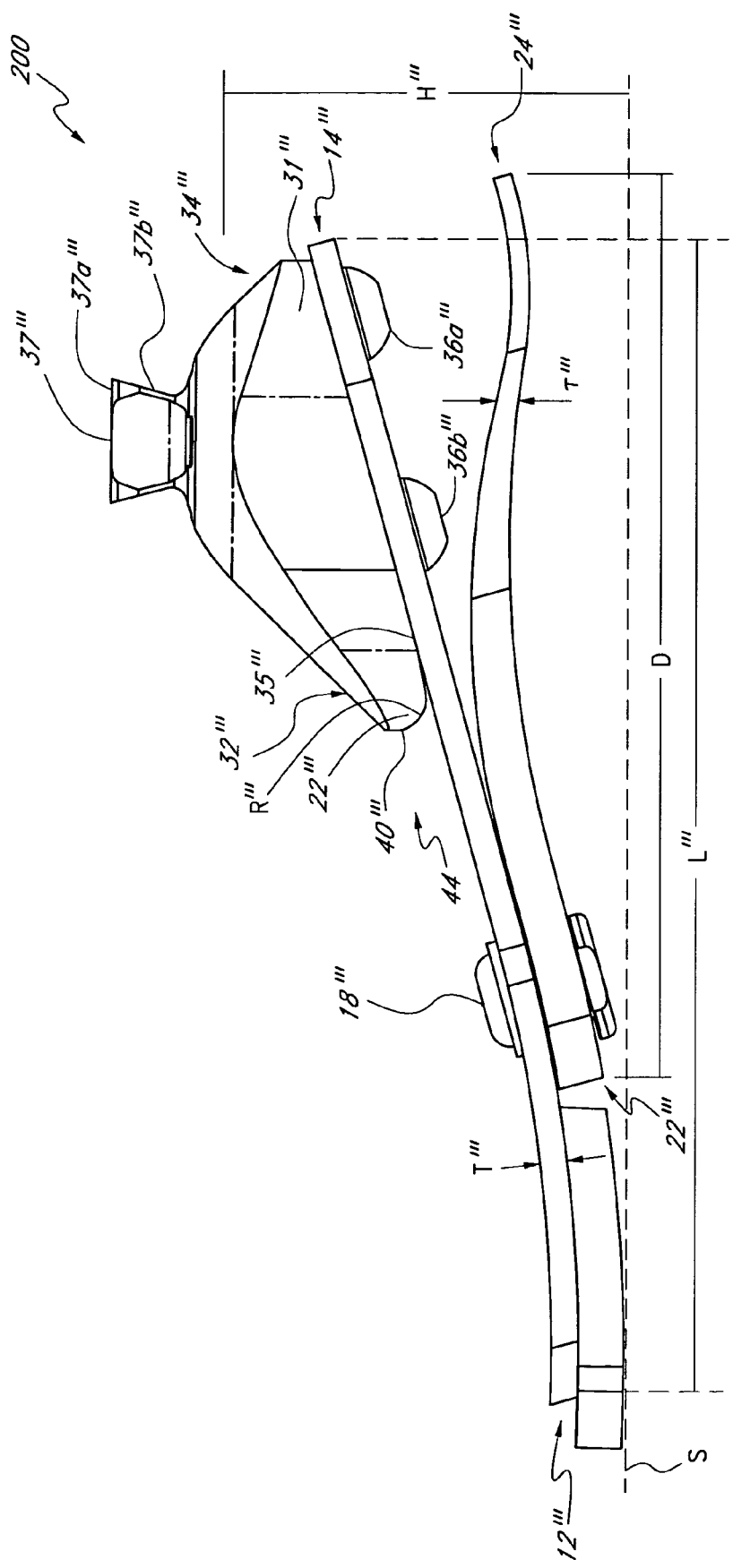
FIG. 9 is a side view of the prosthetic foot illustrated in FIG. 8.

As shown in FIGS. 8-9, the prosthetic foot 200 comprises a foot member 10''', a heel member 20''' extending rearwardly from a point intermediate a front end 12''' and a rear end 14''' of the foot member 10''', and an adapter 30''' mounted to a posterior portion 14a''' of the foot member 10'''. The foot member 10''' has a length L''' of between about 11 and 22 cm, a height H''' of between about 3 and 4 cm, a width W''' between about 4.5 and 6 cm, and a thickness T''' of between about 1.5 and 6 mm. In the illustrated embodiment, the foot member 10''' has a length L''' of about 13 cm, a height H''' of about 3 cm, a width W''' of about 5 cm, and a thickness T''' of about 3 mm. Similarly, the heel member 20''' has a length D of between about 9 and 12.5 cm, a width E of between about 30 and 55 mm, and a thickness τ''' of between about 1.5 and 7 mm. In the illustrated embodiment, the heel member 20''' has a length D of about 10 cm, a width E of about 3.5 cm, and a thickness τ''' that varies between about 5 mm at the front end 22''' and 3 mm at the rear end 24'''. In another embodiment (not shown), the heel member 20''' may have a constant thickness τ'''. Likewise, in some embodiments, the foot member 10''' can have a variable thickness T''' between the front end 12''' and the rear end 14'''.

Figure 10:
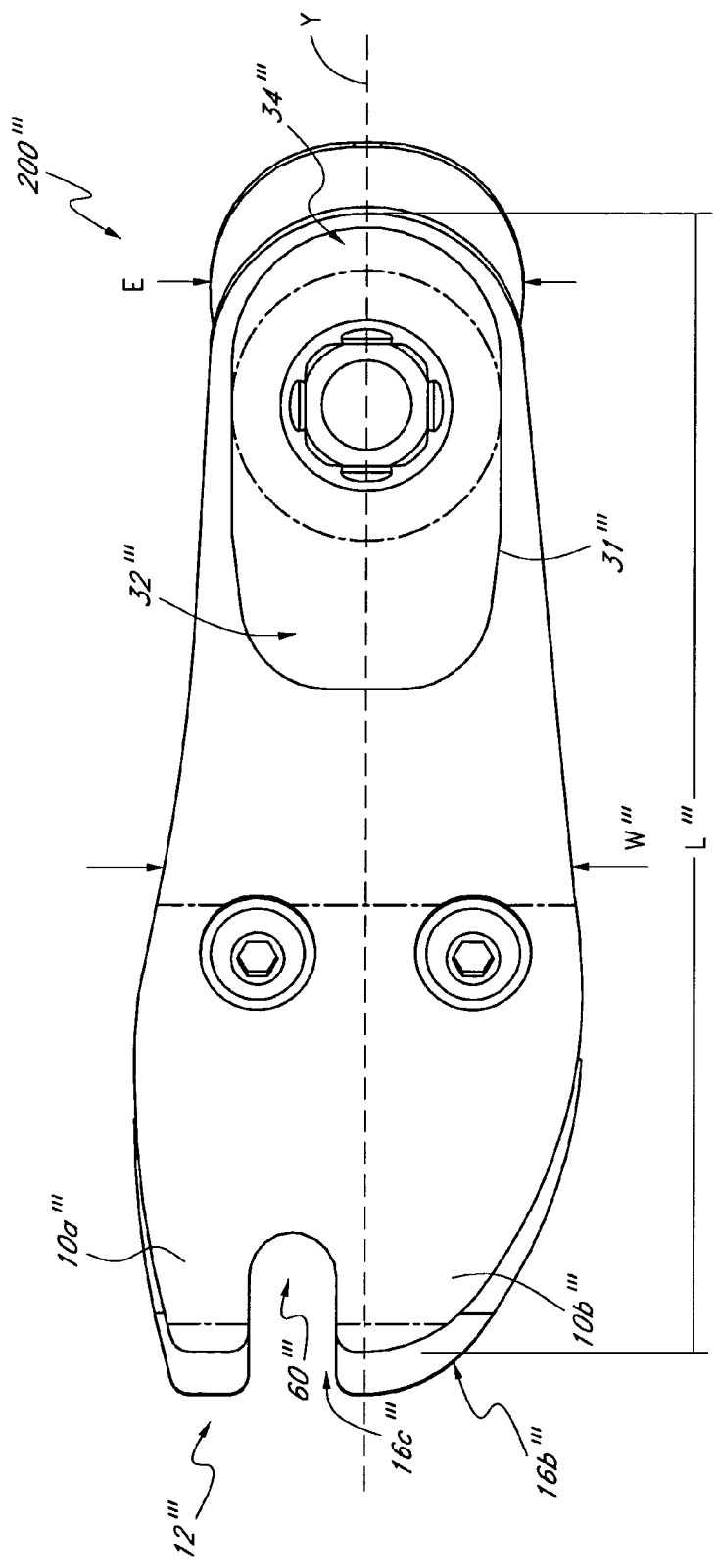
FIG. 10 is a top view of the prosthetic foot illustrated in FIG. 8.
Figure 11:
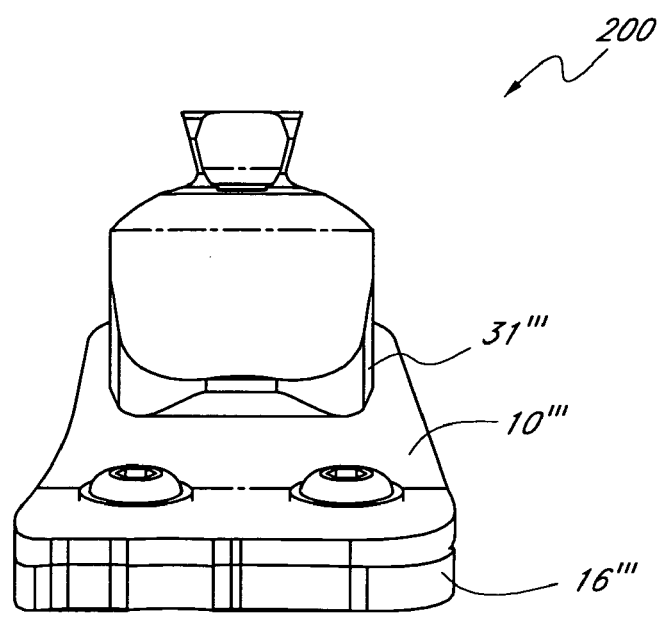
FIG. 11 is a front view of the prosthetic foot illustrated in FIG. 8.

As best seen in FIGS. 8 and 10, in one preferred embodiment, the anterior portion 12a''' of the foot member 10''' comprises at least two toe members 10a''', 10b'''. Said toe members 10a''', 10b''' are preferably defined by at least one longitudinal slot 60''' in the foot member 10''' extending rearwardly from the front end 12'''. In the illustrated embodiment, the longitudinal slot 60''' extends into the foot member 10''' about 3 cm from the front end 12'''. However, the foot member 10''' can be configured to have a slot 60''' extending further into the foot member 10'''. In one embodiment, the slot 60''' is adapted to receive a thong of a sandal or similar footwear. In another embodiment, the slot 60''' is adapted to receive a foot cover with a corresponding slot between the toe members 10a''', 10b''' to provide a more aesthetically pleasing foot cover.

In one preferred embodiment, as best shown in FIGS. 8-10, the prosthetic foot 200 also comprises a crepe portion 16''' attached to the anterior portion 12a''' of the foot member 10'''. As shown in FIG. 10, the crepe portion 16''' has a front end 16b''' that preferably extends forwardly of the front end 12''' of the foot member 10'''. Additionally, the crepe portion 16''' also has a longitudinal slot 16c''' extending through the crepe portion 16'''. Preferably, the slot 16c''' is configured to align with the slot 60''' in the foot member 10'''. In the illustrated embodiment, the slots 60''', 16c''' are offset from an axis Y corresponding to the centerline of the foot member 10'''. In another preferred embodiment, the slots 60''', 16c''' can be aligned with the axis Y.

As shown in FIG. 9, the adapter 30''' has an elongated body 31''' extending between an anterior section 32''' and a posterior section 34'''. The adapter 30''' also has a base 35''', at least a portion of which contacts the foot member 10''' when the adapter 30''' is connected to the foot member 10'''. The adapter 30''' also defines an edge 40''' along the base 35''' at the anterior section 32'''. In the illustrated embodiment, the edge 40''' curves at a radius R''' relative to the base 35''' such that the adapter 30''' is configured to roll-up onto the foot member 10''' during motion of the prosthetic foot 200. The radius of curvature R''' is preferably between about 5 and 10 cm. In the illustrated embodiment, the radius of curvature R''' is about 7 cm. However, as discussed above, the base 35''' need not be curved or have a radius R''' in order for the adapter 30''' to roll-up onto the foot member 10'''. In other embodiments, the base 35''' may comprise generally flat portions or a combination of flat and curved portions, wherein the base 35''' is adapted to move relative to the foot member 10''' during motion of the foot 200. For example, the base 35''' may extend relative to the foot member 10''' so as to define a longitudinal gap (not shown) therebetween. Additionally, as shown in FIG. 10, in one preferred embodiment, the body 31''' of the adapter 30''' tapers from the posterior section 34''' to the anterior section 32'''.

In the embodiment illustrated in FIG. 9, the adapter 30''' is removably attached to the foot member 10''' via adapter connector 36'''. In one embodiment, the connector 36''' may comprise two bolts connecting the adapter 30''' to the foot member 10'''. In another embodiment, the connector 36''' may comprise four bolts. In the illustrated embodiment, a distal connector 36a''' is attached to the posterior section 34''' of the adapter 30''' and a proximal connector 36b''' is attached to the anterior sections 32'''. However, the proximal connector 36b''' is preferably disposed a sufficient distance from a tip 44 of the adapter 30''' to allow the adapter 30''' to roll-up onto the foot member 10'''. In one embodiment, the distance between the proximal connector 36b''' and the tip 44 is about 10% or more of the length of the adapter 30'''. More preferably, the distance between the proximal connector 36b''' and the tip 44 is at least about 20% or more of the length of the adapter 30'''. Still more preferably, the distance between the proximal connector 36b''' and the tip 44 is about 30% or more of the length of the adapter 30'''. In another embodiment, the distance between the proximal connector 36b''' and the tip 44 is about 40% or more of the length of the adapter 30'''. In the illustrated embodiment, the distance between the proximal connector 36b''' and the tip 44 is about 35% of the length of the adapter

30'''. In another embodiment, the adapter 30''' can be permanently attached to the foot member 10''' via, for example, an adhesive, a resin, or the like.

In practice, the prosthetic foot 100 of FIGS. 1-11 advantageously provides a fluid heel-to-toe movement as compared to other prosthetic foot designs. As a user proceeds from heel-strike to toe-off, the adapter 30 rolls-up onto the foot member 10, causing the posterior portion 14a of the foot member 10 to flex toward the anterior portion 12a. In the embodiment described in FIGS. 1-6B above, the roll-up is provided because the adapter 30 is only connected to the foot member 10 at its posterior section 34, leaving the anterior section 32 free to move relative to the foot member 10. However, as described in the embodiment illustrated in FIGS. 8-11, the adapter 30''' can be connected to the foot member 10''' at any location that allows the anterior section 32''' free to more relative to the foot member 10'''. For example, the adapter 30''' can be connected at a point intermediate the anterior and posterior sections 32''', 34''' of the adapter 30'''.

With respect to the embodiments disclosed in FIGS. 1-11, the degree of the roll-up effect is due at least in part to the radius of curvature R of the adapter 30. For example, the smaller the radius of curvature R is, the more pronounced the curved surface of the base 35 is and the greater the roll-up effect. The roll-up effect provides greater flexion of the foot member 10 than a prosthetic foot with a conventional adapter 30, thus providing a more fluid foot motion. Additionally, the radius of curvature R advantageously effects the progressive stiffening of the foot member 10 as the adapter 30 rolls-up onto the member 10. The roll-up effect also provides more efficient energy storage and release during heel-strike through toe-off. However, as discussed above, the adapter 30 need not have a base 35 with a radius R or a curved surface in order to roll-up onto the foot member 10.

Another advantage of the prosthetic foot 100, such as the embodiment shown in FIG. 1, is that its low profile nature allows the prosthetic foot 100 to be used by amputees with long residual limbs as well as amputees with shorter residual limbs. The low profile nature of the foot 100 allows it to be housed completely within a cosmesis 70 (see e.g., FIG. 7) covering the prosthetic foot 100, advantageously providing a more aesthetically pleasing design.

Still another advantage of the prosthetic foot 100 of FIGS. 1-11 is the inclined nature of the foot member 10, as described above, which allows the member 10 to flex during motion of the foot 100. Moreover, the inclined posterior portion 14a advantageously facilitates the flexion of the foot member 10 during roll-up of the adapter 30 thereon, resulting in increased flexion of the foot member 10. This is an improvement over conventional prosthetic foot designs (not shown) that have a rear foot member portion generally horizontal relative to the support surface S, which do not facilitate said foot member flexion. The inclined foot member 10 also allows the prosthetic foot 100 to have a lower build height, in contrast, for example, with prosthetic foot designs that use C-shaped springs and the like. However, the inclined foot member 10 advantageously provides sufficient build height to facilitate access to the adapter 30.

Another advantage of the prosthetic foot 100 in FIGS. 1-7 is its increased strength and reliability relative to conventional designs. Specifically, the prosthetic foot 100 is advantageously rated for use in all impact levels and for amputee weights varying over a wide range. For example, in one preferred embodiment, the prosthetic foot 100 can be used by amputees weighing up to about 165 kg. Additionally, the prosthetic foot 100 is fabricated so that the foot member 10 is stronger than conventional prosthetic foot designs while still being able to flex to provide efficient energy storage and release during motion of the foot 100.

As discussed above, the adapter 30 shown in FIGS. 1-7 is preferably positioned in the posterior 25% of the foot member 10 when the foot member 10 is disposed in the cosmesis 70. Said positioning of the adapter 30 advantageously provides increased deflection of the anterior portion 12a of the foot member 10. Said positioning of the adapter 30 also advantageously allows the adapter 30 to be generally centered relative to an opening in the cosmesis 70 and facilitates the removal of the prosthetic foot 100 from the cosmesis 70. Additionally, the location of the adapter 30 provides easier access to the adapter connectors 36.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus for example, those skilled in the art will recognize that the invention may be embodied or carried out in a manner that achieves or optimizes one advantage or group of advantages as taught herein without necessarily achieving other objects or advantages as may be taught or suggested herein.

The embodiments illustrated in FIGS. 1-11 show the length L, L''' of the foot member 10, 10''' substantially coinciding with the length of the prosthetic foot 100, 200 so that the foot member 10, 10''' extends from heel to toe of the foot 100, 200. However, the foot member 10, 10''' need not extend the full length of the prosthetic foot 100, 200. In some embodiments, the foot member 10, 10''' can extend to a point rearward of the front end of the prosthetic foot 100, 200 and/or connect to another member (not shown) that extends to the front end of the foot 100, 200. The embodiments in FIGS. 1-11 also show the heel member 20, 20''' extending rearward from a point intermediate the front end 12, 12''' and rear end 14, 14''' of the foot member 10, 10'''. However, the heel member 20, 20''' need not extend from a point intermediate the length L, L''' of the foot member 10, 10'''. In some embodiments, the heel member 20, 20''' may extend from the rear end 14, 14''' of the foot member 10, 10'''. In other embodiments, the heel member 20, 20''' may extend from the front end 12, 12''' of the foot member 10, 10'''. In still other embodiments, the front end 12, 12''' of the foot member 10, 10''' may extend from a point intermediate the front end 22, 22''' and the rear end 24''' of the heel member 20, 20''', where the heel member 20, 20''' is generally parallel to the support surface S.

All of these aspects are intended to be within the scope of the invention herein disclosed. These and other aspects of the present invention will become readily apparent to those skilled in the art from the appended claims and from the preceding detailed description of the preferred embodiments having reference to the attached figures, the invention not being limited to any particular preferred embodiment(s) disclosed.

What is claimed is:

1. In combination, an elongate foot support adapted for use in a prosthetic foot and a monolithic adapter mounted to a posterior portion of the foot support, the adapter comprising a pyramid vertically oriented with respect to a support surface on which the foot rests, the pyramid extending along an axis at a non-perpendicular angle relative to the base of the adapter, the adapter having a base with a length contacting the foot support, said base being inclined along substantially the entire length of the adapter from a rearmost end to a frontmost end of the adapter at a constant angle relative to the pyramid and to the support surface, the base in contact with the foot support along substantially the entire length of the adapter from the rearmost end to the frontmost end of the adapter during motion of the prosthetic foot through a complete gait cycle of the prosthetic foot, the base being monolithic with a curved portion at an anterior section of the adapter, the base defining an edge at the anterior section having a radius of curvature of between about 0.5 cm and 4 cm.

2. The combination of claim 1, wherein the anterior section is configured to roll-up along said edge onto the foot support.

3. The combination of claim 1, wherein the edge curls upwardly toward the anterior section of the adapter.

4. The combination of claim 1, wherein the pyramid is a male pyramid.

5. The combination of claim 1, further comprising an elongate heel support below the foot support and a resilient member positioned between the heel support and foot support.

6. The combination of claim 5, wherein the elongate heel support is connected to the foot support, and further comprising a slot between the heel support and the foot support rearward of the connection between the elongate heel support and the foot support.

7. The low profile prosthetic foot of claim 1, wherein the adapter comprises a recessed surface extending at least partially around the circumference of the adapter to thereby decrease the weight of the adapter.

8. A low profile prosthetic foot comprising:
   a foot support extending between a front end and a rear end and having an anterior portion and a posterior portion, the posterior portion inclined at an angle relative to a support surface; and
   a monolithic adapter comprising a pyramid vertically oriented with respect to the support surface, the pyramid extending along an axis at a non-perpendicular angle relative to a base of the adapter, the adapter mounted to the posterior portion of the foot support and having an anterior section, a posterior section, and the base, wherein at least a portion of the base contacts the posterior portion of the foot support, the base being inclined along substantially the entire length of the adapter from a rearmost end to a frontmost end of the adapter at a constant angle relative to the pyramid and to the support surface, the base in contact with the foot support along substantially the entire length of the adapter from the rearmost end to the frontmost end of the adapter during motion of the prosthetic foot through a complete gait cycle of the prosthetic foot, the base being monolithic with a curved section at the anterior section of the adapter, the base defining an edge at the anterior section having a radius of curvature of between about 0.5 cm and 4 cm, the anterior section configured to move relative to the foot support.

9. The prosthetic foot of claim 8, further comprising a heel support operatively connected to the foot support.

10. The prosthetic foot of claim 9, wherein the heel support is directly connected to the foot support.

11. The prosthetic foot of claim 9, further comprising a resilient member between the foot support and the heel support.

* * * * *

UNITED STATES PATENT AND TRADEMARK OFFICE
CERTIFICATE OF CORRECTION

PATENT NO. : 8,007,544 B2  
APPLICATION NO. : 10/642125  
DATED : August 30, 2011  
INVENTOR(S) : Orn Ingvi Jonsson et al.

Page 1 of 1

It is certified that error appears in the above-identified patent and that said Letters Patent is hereby corrected as shown below:

At column 11, line 37, please delete ""'"" and insert --"'"".--, therefor.

Signed and Sealed this
Twelfth Day of March, 2013

Teresa Stanek Rea
*Acting Director of the United States Patent and Trademark Office*